US012679798B2

(12) United States Patent
Kramp et al.

(10) Patent No.: US 12,679,798 B2
(45) Date of Patent: *Jul. 14, 2026

(54) CONTINUOUS METHOD FOR PRODUCING N-BUTYL(METH)ACRYLATE INCLUDING A CATALYST RECIRCULATION PROCESS

(71) Applicant: BASF SE, Ludwigshafen am Rhein (DE)

(72) Inventors: Marvin Kramp, Ludwigshafen am Rhein (DE); Ortmund Lang, Ludwigshafen am Rhein (DE); Josef Macht, Ludwigshafen am Rhein (DE); Asyraf Thevendran Bin Abdullah, Kuantan (MY); Christine Carola Behrens, Ludwigshafen am Rhein (DE); Cornelis Hendricus De Ruiter, Ludwigshafen am Rhein (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

This patent is subject to a terminal disclaimer.

(21) Appl. No.: 19/101,657

(22) PCT Filed: Aug. 7, 2023

(86) PCT No.: PCT/EP2023/071760
§ 371 (c)(1),
(2) Date: Feb. 6, 2025

(87) PCT Pub. No.: WO2024/033279
PCT Pub. Date: Feb. 15, 2024

(65) Prior Publication Data
US 2025/0257026 A1     Aug. 14, 2025

(30) Foreign Application Priority Data
Aug. 8, 2022    (EP) .................................... 22189268

(51) Int. Cl.
*C07C 67/08* (2006.01)
*C07C 67/54* (2006.01)
*C07C 67/62* (2006.01)

(52) U.S. Cl.
CPC .............. *C07C 67/08* (2013.01); *C07C 67/54* (2013.01); *C07C 67/62* (2013.01)

(58) Field of Classification Search
CPC ......... C07C 67/08; C07C 67/54; C07C 67/62; C07C 69/54
See application file for complete search history.

(56) References Cited

U.S. PATENT DOCUMENTS 5,883,288 A * 3/1999 Iffland .................... C07C 67/08
560/205
6,084,122 A * 7/2000 Garza, Jr. .............. C07C 67/58
560/218
(Continued)

FOREIGN PATENT DOCUMENTS

DE      19604267 A1     8/1997
DE      69817858 T2     7/2004
(Continued)

OTHER PUBLICATIONS

European Search Report for EP Patent Application No. 22189268.0, Issued on Jan. 30, 2023, 3 pages.
(Continued)

*Primary Examiner* — Andrew D Kosar
*Assistant Examiner* — Blaine G Doletski
(74) *Attorney, Agent, or Firm* — Faegre Drinker Biddle & Reath LLP

(57) ABSTRACT

The invention relates to a method for continuously producing n-butyl(meth)acrylate by reacting (meth)acrylic acid with n-butanol in the presence of an acid catalyst and a polymerization inhibitor. In a first embodiment, the method has the steps of: * carrying out an esterification within a reactor (A) comprising a column (B) installed thereon, wherein the components (meth)acrylic acid and n-butanol are used in a molar ratio ranging from 1.0:1.0 to 10:2.0, preferably 1.0:1.1 to 1.0:1.5, and the esterification is carried out at a temperature ranging from 80 to 150° C., preferably 100 to 130° C., and an absolute pressure ranging from 0.2 to 5.0 bar, preferably 0.4 to 1.5 bar, whereby a resulting reaction product (6) and a vapor flow are obtained at the head of the column (B), * discharging the vapor flow at the head of the column (B), * condensing the vapor flow in a condenser (C), thereby forming an organic phase, which is enriched with n-butyl(meth)acrylate, and an aqueous phase, * continuously separating the organic phase from the aqueous phase by means of a phase separator (D), * supplying the resulting reaction product (6) to a rectification column (E), * separating the azeotrope within the rectification column (E) consisting of: a) water and n-butyl(meth)acrylate, b) n-butanol and n-butyl(meth)acrylate, c) n-butanol and water, and d) n-butanol, n-butyl(meth)acrylate, and water, wherein the rectification column (E) is operated at a sump temperature ranging from 80 to 150° C. and at a temperature at the head ranging from 70 to 130° C. and an absolute pressure ranging from 0.2 to 5 bar, preferably 0.4 to 1.5 bar, * discharging a gas flow enriched with the azeotrope at the head of the rectification column (E), * condensing the gas flow in a condenser (F), thereby forming an organic phase, which is enriched with n-butyl(meth)acrylate, and an aqueous phase, * continuously separating the organic phase from the aqueous phase by means of a phase separator (G), * continuously discharging at least one part of the organic
(Continued)

phase out of the phase separator (G), said discharged part of the n-butyl(meth)acrylate-enriched organic phase constituting the raw product flow (15), * discharging a high-boiling sump discharge (23) out of the sump of the rectification column (E), the mass flow ratio of the high-boiling sump discharge (23) to the (meth)acrylic acid supplied to the reactor (A) as a reactant ranging from 0.5 to 5, * supplying a high-boiling sub-flow (7) of the discharged high-boiling sump discharge (23) to a mixer (H), the mass flow ratio of the high-boiling sub-flow (7) to the high-boiling sump discharge (23) ranging from 0.01 to 0.5, preferably 0.05 to 0.08, * supplying a mixture (10) resulting from the mixer (H) to an extraction phase separator (I) arranged downstream thereof, and * continuously separating the mixture in the extraction phase separator (I), thereby obtaining an organic raffinate (11) and an aqueous catalyst-containing extract (12), said aqueous extract (12) being at least partly recirculated to the reactor (A) and/or the rectification column (E), wherein —a sub-flow of the aqueous phase (18) from the phase separator (G), —a sub-flow of the aqueous phase (26) from the phase separator (D) and/or —a sub-flow of the aqueous phase (5) from the phase separator (D) is supplied to the phase separator (G), and subsequently a sub-flow of the aqueous phase (18) from the phase separator (G) is supplied to the mixer (H). The mass flow ratio of the sub-flow of the aqueous phase (18) to the high-boiling sub-flow (7) of the discharged high-boiling sump discharge (23) ranges from 0.08 to 0.50, and the mass flow ratio of the sub-flow of the aqueous phase (5) to the high-boiling sub-flow (7) of the discharged high-boiling sump discharge (23) ranges from 0.08 to 0.50.

13 Claims, 3 Drawing Sheets

(56)                    References Cited

U.S. PATENT DOCUMENTS

| | | | | |
|---|---|---|---|---|
| 6,084,128 A | * | 7/2000 | Warner | .................. C07C 67/58 |
| | | | | 562/600 |
| 2013/0085291 A1 | * | 4/2013 | Ko | .......................... C07C 67/54 |
| | | | | 560/205 |

FOREIGN PATENT DOCUMENTS

| | | |
|---|---|---|
| EP | 0795536 A1 | 9/1997 |
| WO | 01/19772 A1 | 3/2001 |
| WO | 2012/026661 A1 | 3/2012 |

OTHER PUBLICATIONS

International Preliminary Report on Patentability received for PCT Patent Application No. PCT/EP2023/071760, mailed on Jul. 12, 2024, 23 pages (8 pages of English Translation and 15 pages of Original Document).
International Search Report and Written Opinion received for PCT Patent Application No. PCT/EP2023/071760, mailed on Nov. 16, 2023, 18 pages (2 pages of English Translation and 16 pages of Original Document).

* cited by examiner

CONTINUOUS METHOD FOR PRODUCING N-BUTYL(METH)ACRYLATE INCLUDING A CATALYST RECIRCULATION PROCESS

CROSS-REFERENCE TO RELATED APPLICATIONS

This application is a National stage application (under 35 U.S.C. § 371) of PCT/EP2023/071760, filed Aug. 7, 2023, which claims benefit of European Application No. 22189268.0, filed Aug. 8, 2022, both of which are incorporated herein by reference in their entirety.

The present invention relates to a process for continuously preparing n-butyl (meth)acrylate by reacting (meth)acrylic acid with n-butanol in the presence of an acidic catalyst and a polymerization inhibitor.

n-Butyl (meth)acrylate finds use particularly advantageously in the production of contact lenses or as crosslinker or adhesion improver for dispersions that are preferably used as adhesives, paints, inks, for example including printing inks, for textile, leather or paper auxiliaries, and in curable coatings.

In esterifications of alkanol with acid, typical equilibrium reactions are generally proceeding, which are catalyzed by strong acids and which, as typical condensation reactions, lead to the elimination of water of esterification. Typically, removing the water of esterification from the reaction mixture shifts the esterification equilibrium in the direction of the forward reaction, which increases the conversion rates for the target product.

The acidic catalysts that are typically used for the esterification reaction include inorganic acids such as sulfuric acid, organic acids such as alkanesulfonic acids, ion exchange resins and the like.

The water of esterification can be removed by distillation as a constituent of an azeotrope that also typically comprises the target ester. In general, the esterification reaction is effected in such a way that the water of esterification is removed continuously from the reaction mixture, although the majority of the target ester formed remains in the reaction mixture.

Examples of esterifications of this kind are those in which the water of esterification is removed by distillation by addition of an organic solvent as azeotropic entraining agent. It is also possible for alkanol used in excess to serve as such an azeotropic entraining agent.

In one variant for preparation of n-butyl (meth)acrylate, the water of esterification is separated off by distillation as a constituent of a heterogeneous azeotrope of n-butyl (meth) acrylate/n-butanol/water, and the n-butanol and/or the n-butyl (meth)acrylate is recycled at least partly into the esterification as organic phase.

A challenge with this method is that the water of esterification that forms in the esterification has to be at least partly discharged from the process. Moreover, the discharged proportion of catalyst is typically incinerated, which gives rise to unwanted $SO_x$ emissions in the case of use of sulfuric or sulfonic acids, for example.

A process for continuously preparing alkyl esters of (meth)acrylic acid with recycling of an acidic catalyst into the reaction zone of the reactor is disclosed by EP 0795 536 A1 (BASF AG). This document elucidates recycling of the acidic catalyst only for the alkyl ester 2-ethylhexyl acrylate (2-EHA). There is no disclosure of applicability and transferability of this teaching to the other physical process conditions in the preparation of n-butyl acrylate and the esterification reaction that takes place here with a downstream specific purification to give the alkyl ester n-butyl acrylate.

A process for continuously preparing alkyl (meth)acrylate, especially n-butyl acrylate, is disclosed by WO 2012/026661 A1 (LG Chem, LTD.). In this process, an organic acidic catalyst is recycled into the reaction zone of the reactor. However, the recycling is limited in that the mass flow of the bottoms outlet from the rectification column is already biphasic. Thus, the mass flow of the bottoms outlet from the rectification column already comprises an organic phase and an aqueous phase.

The problem addressed was therefore that of providing a continuous process for preparing n-butyl (meth)acrylate with catalyst recycling in order to enable improvement in the recovery rate of the catalyst during the preparation of the n-butyl (meth)acrylate using an acidic catalyst. This also reduces the amount of the catalyst discharged.

A further problem addressed was that of carrying as small as possible an amount of water through the esterification and the distillative purification in order to make the process energy-efficient. An associated effect is that a small amount of secondary components is formed in the process, since the reaction mixture is exposed to lower temperatures in the process.

An additional problem addressed was that of achieving a greater conversion and a greater yield of n-butyl (meth) acrylate.

In this document, the reference numbers in brackets serve for better understanding when reading. The reference numbers in brackets have no limiting effect, but merely constitute one possible example in each case of multiple implementation options.

The process according to the invention is based on the reactants n-butanol and (meth)acrylic acid. In this document, (meth)acrylic acid is used to refer to a (meth)acrylic acid quality which preferably includes at least 98% by weight, more preferably at least 99.5% by weight, of (meth)acrylic acid, and in addition preferably has not more than 0.2% by weight of water and also preferably not more than 0.03% by weight in each case of acetic acid, propionic acid and isobutyric acid. Preference is given to using an n-butanol quality with at least 99.5% by weight of n-butanol, not more than 0.05% by weight of n-butanal, not more than 0.02% by weight of dibutyl ether, not more than 0.1% by weight of other alcohols, and not more than 0.05% by weight of water. The color number is preferably not more than APHA 5, and the acid number preferably not more than 0.03 mgKOH/g.

Suitable polymerization inhibitors that act as stabilizers may be, for example, N-oxides (nitroxyl or N-oxyl radicals, i.e. compounds having at least one NO group) such as 4-hydroxy-2,2,6,6-tetramethylpiperidine N-oxyl (HO-TEMPO), 4-oxo-2,2,6,6-tetramethylpiperidine N-oxyl, 4-acetoxy-2,2,6,6-tetramethylpiperidine N-oxyl, 2,2,6,6-tetramethylpiperidine N-oxyl, bis(1-oxyl-2,2,6,6-tetramethylpiperidin-4-yl) sebacate, 4,4',4"-tris(2,2,6,6-tetramethylpiperidine N-oxyl) phosphite or 3-oxo-2,2,5,5-tetramethylpyrrolidine N-oxyl; monohydric or polyhydric phenols optionally having one or more alkyl groups, such as alkylphenols, for example o-, m- or p-cresol (methylphenol), 2-tert-butylphenol, 4-tert-butylphenol, 2,4-di-tert-butylphenol, 2-methyl-4-tert-butylphenol, 2-tert-butyl-4-methylphenol, 2,6-tert-butyl-4-methylphenol, 4-tert-butyl-2,6-dimethylphenol or 6-tert-butyl-2,4-dimethylphenol; quinones such as hydroquinone, hydroquinone monomethyl ether, 2-methylhydroquinone or 2,5-ditert-butylhydroquinone; hydroxyphenols such as catechol (1,2-dihydroxybenzene) or benzoquinone; aminophenols such as p-aminophenol; nitrosophenols such as p-nitrosophenol; alkoxyphenols such as 2-methoxyphenol (guaiacol, catechol monomethyl ether), 2-ethoxyphenol, 2-isopropoxyphenol, 4-methoxyphenol (hydroquinone monomethyl ether), mono- or di-tert-butyl-4-methoxyphenol; tocopherols such as α-tocopherol and 2,3-dihydro-2,2-dimethyl-7-hydroxybenzofuran (2,2-dimethyl-7-hydroxycoumaran), aromatic amines such as N,N-diphenylamine or N-nitrosodiphenylamine; phenylenediamines such as N,N'-dialkyl-p-phenylenediamine, where the alkyl radicals may be the same or different and each independently consist of 1 to 4 carbon atoms and may be straight-chain or branched, for example N,N'-dimethyl-p-phenylenediamine or N,N'-diethyl-p-phenylenediamine, hydroxylamines such as N,N-diethylhydroxylamine, imines such as methylethylimine or methylene violet, sulfonamides such as N-methyl-4-toluenesulfonamide or N-tert-butyl-4-toluenesulfonamide, oximes such as aldoximes, ketoximes or amidoximes such as diethyl ketoxime, methyl ethyl ketoxime or salicylaldoxime, phosphorus compounds such as triphenylphosphine, triphenyl phosphite, triethyl phosphite, hypophosphorous acid or alkyl esters of phosphorous acids; sulfur compounds such as diphenyl sulfide or phenothiazine; metal salts such as salts of copper or manganese, of cerium, of nickel, and of chromium, for example chlorides, sulfates, salicylates, tosylates, acrylates or acetates, for example copper acetate, copper (II) chloride, copper salicylate, cerium (III) acetate or cerium (III) ethylhexanoate, or mixtures thereof.

The polymerization inhibitor or polymerization inhibitor mixture used is preferably at least one compound from the group of hydroquinone, hydroquinone monomethyl ether, phenothiazine, 4-hydroxy-2,2,6,6-tetramethylpiperidine N-oxyl, 4-oxo-2,2,6,6-tetramethylpiperidine N-oxyl, bis(1-oxyl-2,2,6,6-tetramethylpiperidin-4-yl) sebacate, 2-tert-butylphenol, 4-tert-butylphenol, 2,4-di-tert-butylphenol, 2-tert-butyl-4-methylphenol, 6-tert-butyl-2,4-dimethylphenol, 2,6-di-tert-butyl-4-methylphenol, 2-methyl-4-tert-butylphenol, hypophosphorous acid, copper (II) acetate, copper (I) chloride, copper (II) chloride, copper (II) salicylate and cerium (III) acetate.

Particular preference is given to using phenothiazine (PTZ) and/or hydroquinone monomethyl ether (MEHQ) as polymerization inhibitor.

Very particular preference is given to using PTZ as polymerization inhibitor in the esterification and/or in the distillation.

The polymerization inhibitor is preferably dissolved in one or more liquid organic compounds. The organic compound is preferably n-butanol and/or n-butyl (meth)acrylate.

Useful esterification catalysts include the standard mineral acids and sulfonic acids, preferably sulfuric acid, phosphoric acid, alkylsulfonic acids (e.g. methanesulfonic acid, trifluoromethanesulfonic acid) and arylsulfonic acids (e.g. benzenesulfonic acid, p-toluenesulfonic acid or dodecylbenzenesulfonic acid) or mixtures thereof.

Particular preference is given to sulfuric acid, methanesulfonic acid, p-toluenesulfonic acid, m-toluenesulfonic acid, o-toluenesulfonic acid or mixtures thereof.

Very particular preference is given to using p-toluenesulfonic acid as esterification catalyst.

The acidic catalyst is especially a homogeneous catalyst. The acidic catalyst used is preferably sulfuric acid, phosphoric acid, alkylsulfonic acids (e.g. methanesulfonic acid, trifluoromethanesulfonic acid) and arylsulfonic acid (e.g. benzene-, p-toluene- or dodecylbenzenesulfonic acid) or mixtures thereof, further preferably p-toluenesulfonic acid.

According to the invention, the process for continuously preparing n-butyl (meth)acrylate by reacting (meth)acrylic acid with n-butanol in the presence of an acidic catalyst and a polymerization inhibitor comprises the steps of:

performing an esterification within a reactor (A) with a column (B) on top, where the (meth)acrylic acid and n-butanol components are used in a molar ratio in the range from 1.0:1.0 to 1.0:2.0, preferably in the range from 1.0:1.1 to 1.0:1.5, and where the esterification takes place at a temperature in the range from 80 to 150° C., preferably in the range from 100 to 130° C., and at an absolute pressure in the range from 0.2 to 5.0 bar, preferably in the range from 0.4 to 1.5 bar, as a result of which a resulting reaction output (6) and a vapor stream are obtained at the top of the column (B), discharging the vapor stream at the top of the column (B), condensing the vapor stream in a condenser (C) to form an organic phase and an aqueous phase, continuously separating the organic phase from the aqueous phase by means of a phase separator (D), feeding the resulting reaction output (6) into a rectification column (E), removing the following azeotropes within the rectification column (E):

a) water and n-butyl (meth)acrylate, b) n-butanol and n-butyl (meth)acrylate, c) n-butanol and water, d) n-butanol, n-butyl (meth)acrylate and water, where the rectification column (E) is operated at a bottom temperature in the range from 80 to 150° C. and at a temperature at the top in the range from 70 to 130° C. and at an absolute pressure in the range from 0.2 to 5 bar, discharging a gas stream enriched by the azeotropes at the top of the rectification column (E), condensing the gas stream in a condenser (F) to form an n-butyl (meth)acrylate-enriched organic phase and an aqueous phase, continuously separating the organic phase from the aqueous phase by means of a phase separator (G), continuously removing at least a portion of the organic phase and the phase separator (G), where this removed portion of the n-butyl (meth)acrylate-enriched organic phase constitutes the crude product stream (15), discharging a high boiler bottoms output (23) from the bottom of the rectification column (E), where the mass flow ratio between the high boiler bottoms output (23) and the (meth)acrylic acid (1) fed to the reactor (A) as reactant is in the range from 0.5 to 5, feeding a high boiler substream (7) of the discharged high boiler bottoms output (23) into a mixer (H), where the mass flow ratio between the high boiler substream (7) and the high boiler bottoms output (23) is in the range from 0.01 to 0.50, preferably in the range from 0.05 to 0.08, feeding a mixture (10) that results from the mixer (H) into a downstream extraction phase separator (I), continuously separating off the mixture (10) in the extraction phase separator (I) to obtain an organic raffinate (11) and a catalyst-comprising aqueous extract (12), where the aqueous extract (12) is recycled at least partly to the reactor (A) and/or to the rectification column (E), wherein a substream of the aqueous phase (18) from the phase separator (G), a substream of the aqueous phase (26) from the phase separator (D) and/or a substream of the aqueous phase (5) and the phase separator (D) is fed to the phase separator (G) and then a substream of the aqueous phase (18) from this phase separator (G)

is fed to the mixer (H), where the mass flow ratio between the substream of the aqueous phase (18) and the high boiler substream (7) of the discharged high boiler bottoms output (23) is in the range from 0.08 to 0.50, and where the mass flow ratio between the substream of the aqueous phase (26) and the high boiler substream (7) of the discharged high boiler bottoms output (23) is in the range from 0.08 to 0.50, preferably in the range from 0.1 to 0.3.

It has been recognized that, surprisingly, the feeding of a substream of the aqueous phase (18) from the phase separator (G) and/or the feeding of a substream of the aqueous phase (26) from the phase separator (D) to the mixer (H) means that the resulting mixture (10) always breaks down into two phases after the starting phase of the plant. As a result, it is always possible to recycle the catalyst under all states of operation that occur in the plant. In addition, the water content within the plant, for example in the reactor (A) or in the rectification column (E), can also be kept at a minimum. Moreover, this makes the process more energy-efficient, and a lower level of secondary components is formed in the process. Moreover, a greater conversion and a greater yield of n-butyl (meth)acrylate is achieved.

In an alternative process of the invention for continuously preparing n-butyl (meth)acrylate by reacting (meth)acrylic acid with n-butanol in the presence of an acidic catalyst and a polymerization inhibitor, the following steps are encompassed:

performing an esterification in a reaction zone (E1), where the reaction zone (E1) is in the bottom of a rectification column (E), where the (meth)acrylic acid and n-butanol components are used in a molar ratio in the range from 1.0:1.0 to 1.0:2.0, preferably in the range from 1.0:1.1 to 1.0:1.5, and where the esterification takes place at a temperature in the range from 80 to 150° C., preferably in the range from 100 to 130° C., and at an absolute pressure in the range from 0.2 to 5.0 bar, preferably in the range from 0.4 to 1.5 bar, removing the following azeotropes that form as a result of the esterification:

a) water and n-butyl (meth)acrylate, b) n-butanol and n-butyl (meth)acrylate, c) n-butanol and water, d) n-butanol, n-butyl (meth)acrylate and water, where the removal takes place by means of the rectification column (E), which is operated at a bottom temperature in the range from 80 to 150° C. and at a temperature at the top in the range from 70 to 130° C. and at an absolute pressure in the range from 0.2 to 5 bar, discharging a gas stream enriched by the azeotropes at the top of the rectification column (E), condensing the gas stream in a condenser (F) to form an n-butyl (meth)acrylate-enriched organic phase and an aqueous phase, continuously separating the organic phase from the aqueous phase by means of a phase separator (G), continuously removing at least a portion of the organic phase and the phase separator (G), where this removed portion of the n-butyl (meth)acrylate-enriched organic phase constitutes the crude product stream (15), discharging a high boiler bottoms output (23) from the bottom of the rectification column (E), where the mass flow ratio between the high boiler bottoms output (23) and the (meth)acrylic acid fed to the reaction zone (E1) as reactant is in the range from 0.05 to 0.5, feeding a high boiler substream (7) of the discharged high boiler bottoms output (23) into a mixer (H), where the mass flow ratio between the high boiler substream (7) and the high boiler bottoms output (23) is in the range from 0.01 to 1.0, preferably in the range from 0.10 to 0.70, feeding a mixture (10) that results from the mixer (H) into a downstream extraction phase separator (I), continuously separating off the mixture (10) in the extraction phase separator (I) to obtain an organic raffinate (11) and a catalyst-comprising aqueous extract (12), where the aqueous extract (12) is recycled at least partly to the rectification column (E), wherein a substream of the aqueous phase (18) from the phase separator (G) is fed to the mixer (H), where the mass flow ratio between the substream of the aqueous phase (18) from the phase separator (G) and the high boiler substream (7) of the discharged high boiler bottoms output (23) is in the range from 0.08 to 0.50, preferably in the range from 0.1 to 0.3.

In this alternative process of the invention, it is also possible to observe the same technical effects. Here too, it has been recognized that the feeding of a substream of the aqueous phase (18) from the phase separator (G) to the mixer (H) means that the resulting mixture (10) always breaks down into two phases after the starting phase of the plant. As a result, it is always possible to recycle the catalyst under all states of operation that occur in the plant. In addition, the water content within the plant, for example in the reaction zone (E1) or in the rectification column (E), can also be kept at a minimum. Thus, the process is more energy-efficient, and a lower level of secondary components is formed in the process. Moreover, a greater conversion and a greater yield of n-butyl (meth)acrylate is achieved.

The term "rectification column" in this document is to be considered to be a general term for apparatuses in which vapors are generated by supply of heat, which ascend and come into contact with liquid phase flowing downward.

Rectification columns are known in terms of their general design and have the customary apparatuses, for example an evaporator in the bottom, an evaporator in the high boiler outlet or a condenser in the low boiler outlet, where the high boilers are preferably in the bottom region and the low boilers preferably in the top region of the rectification column. A portion of the mass flow from the high boiler outlet is typically fed back into the bottom region of the rectification column. However, it is also possible in principle that the bottom region is heated, for example, via an outer wall heating of the column in the bottom region and/or an evaporator is integrated into the bottom region. Typically, a vapor stream is drawn off at the top of the rectification column and fed to a condenser. The vapor stream is also typically referred to as low boiler output. A portion of the vapor stream condensed in the condenser is returned to the rectification column, whereas the remaining portion of the condensed vapor stream is discharged as distillate. The reflux ratio here describes the ratio between the condensed vapor stream which is returned to the column and the condensed vapor stream which is drawn off as distillate. In general, a reflux ratio in the range from 10% to 200% is established. The column internals used for the rectification column (E) may in principle be any standard internals, for example trays, structured packings and/or random packings. Among the trays, preference is given to bubble-cap trays, sieve trays, valve trays, Thormann trays and/or dual-flow trays; among the random packings, preference is given to those comprising rings, spirals, saddles or braids. In addition, the rectification column (E) may also comprise further standard components for regulation, by way of example pressure reducers, flow regulators or sensors. In principle, it is also possible to connect multiple rectification columns to one another by series or parallel connection, which can then also act collectively as a "rectification column" (E).

In this document, in the case of use of acrylic acid, components are referred to as low boilers if the boiling temperature at standard pressure is lower than the boiling temperature of n-butyl acrylate. Analogously, components are referred to as high boilers if the boiling temperature at standard pressure is greater than or equal to the boiling temperature of n-butyl acrylate. The boiling temperature of n-butyl acrylate is 147° C. at standard pressure.

In this document, in the case of use of methacrylic acid, components are referred to as low boilers when the boiling temperature at standard pressure is lower than the boiling temperature of n-butyl methacrylate. Analogously, components are referred to as high boilers if the boiling temperature at standard pressure is greater than or equal to the boiling temperature of n-butyl methacrylate. The boiling temperature of n-butyl methacrylate is 163° C. at standard pressure.

In this document, the term "reactor" generally defines one reactor (A) or else two or more mutually interconnected reactors that act as one "reactor" (A). The reactor (A) additionally comprises a reactor heating element in order to heat the reaction mixture. The reactor heating element is, for example, an immersion heater in the reactor (A), a tube system comprising coiled tubes or half-coiled tubes disposed on the outer jacket surface of the reactor and/or within the reactor (A), an electrical heating system disposed on the outer jacket surface of the reactor (A) and/or within the reactor (A), an evaporator outside the reactor (A), where the reaction mixture flows at least partly through the evaporator, or a jacketed design of the outer reactor wall, in which a fluid separated from the reaction mixture, such as a liquid, a gas and/or a heating steam, is under temperature control and hence a predetermined heating temperature is set, whereby the reaction mixture in the reactor (A) is heated. Two or more reactor heating elements may generally be used to heat the reaction mixture in the reactor (A). For instance, a jacketed design of the outer reactor wall and an evaporator outside the reactor (A) may be used to heat the reaction mixture simultaneously or at least partly with a time delay. In addition, the reactor (A) comprises a column (B) on top, which preferably separates off water by distillation. The column (B) itself is a distillation column with internals. Such internals are trays, such as bubble cap trays, perforated trays, especially dual-flow trays, random packings, structured packings or the like. In a further preferred embodiment, the reactor (A) is integrated into the rectification column (E), such that the esterification can take place in the bottom of the rectification column (E), i.e. in the reaction zone (E1).

In this document, the term "mass flow ratio" between a real numerical value A1 and a real numerical value B1 is equivalent to the division ratio with A1 in the numerator and B1 in the denominator. Thus, the following formula is applicable:

$$\text{Mass flow ratio} = \frac{A1}{B1}.$$

The term "external water" in this document is understood to mean a water that originates from outside the process and is introduced into the process by an inlet in a mixer (H). The external water is preferably a demineralized water, more preferably a fully demineralized water. The external water preferably has a pH in the range from 4.5 to 10.5, more preferably in the range from 6.5 to 10.0. Preferably, the external water includes only a low level of electrolyte components, if any, preferably less than 0.1% by weight of electrolyte components.

The acidic esterification catalyst, i.e. acidic catalyst, used is preferably para-toluenesulfonic acid. The content thereof in the reaction zone (E1) or in the reactor (A) based on the reaction mixture present therein is appropriately 0.1% to 10.0% by weight, preferably 0.1% to 6.0% by weight. Other organic sulfonic acids such as methanesulfonic acid, benzenesulfonic acid, dodecylbenzenesulfonic acid and/or sulfuric acid are likewise usable. The amount thereof is equimolar to that of para-toluenesulfonic acid. Corresponding mixtures are also possible. The content of catalytically active acid in the bottom of the rectification column (E) based on the mixture present therein may advantageously be between 2.5% and 50.0% by weight of para-toluenesulfonic acid or an equivalent amount of another organic sulfonic acid and/or sulfuric acid.

In a preferred configuration of the process, the resulting mixture (10) from the mixer (H) is at a temperature in the range from 20 to 100° C., preferably in the range from 70 to 95° C., at the outlet of the mixer (H). This results in the advantage that both the aqueous phase and the organic phase need not be heated later on in the process and hence energy can be saved.

In a preferred configuration of the process, the high boiler bottoms output (23) has a concentration of less than 10% by weight, preferably less than 5% by weight, of water. This results in the advantage that less water has to be distilled off in the rectification column (E) and hence less energy is consumed for heating of the rectification column (E), as a result of which there is also a lower level of secondary components formed.

In a preferred configuration of the process, a substream of the aqueous extract is returned to the reactor (A) or to the reaction zone (E1), where the mass flow ratio between the substream of the aqueous extract and the total mass flow rate of the aqueous extract (12) is in the range from 0.1 to 1.0, preferably in the range from 0.8 to 1.0. This results in the advantage that the catalyst can be returned efficiently without increasing the water content in the plant.

In a preferred configuration of the process, there is added to the high boiler substream (7) of the discharged high boiler bottoms output (23) in the mixer (H) such a mass flow rate of the substream of the aqueous phase (18) from the phase separator (G) and/or of the substream of the aqueous phase (26) from the phase separator (D) that a phase ratio between the aqueous extract (12) to be obtained and the organic raffinate (11) to be obtained in the range from 0.08 to 0.5 kg/kg, preferably in the range from 0.1 to 0.3 kg/kg, is achieved. This results in the advantage that a biphasic separation of the two phases is assured, as small amount as possible of catalyst has to be discharged from the process, and the water content is minimized in the esterification and in the distillation.

A mass flow ratio between the substream of the aqueous phase (18) and the high boiler substream (7) of the discharged high boiler bottoms output (23) or a mass flow ratio between the substream of the aqueous phase (26) and the high boiler substream (7) of the discharged high boiler bottoms output (23) of 0.5 kg/kg or less is sufficient for the successful recovery of the acidic catalyst and lowers the energy requirement of the process, especially for evaporation of water, compared to the use of greater amounts of water. A mass flow ratio between the substream of the aqueous phase (18) and the high boiler substream (7) of the discharged high boiler bottoms output (23) or a mass flow ratio between the substream of the aqueous phase (26) and the high boiler substream (7) of the discharged high boiler bottoms output (23) of at least 0.08 kg/kg serves in turn for effective extraction and phase separation in the extraction phase separator (I).

In a preferred configuration of the process, at least a substream of the organic raffinate (11) is fed to a cleavage reactor (J). In particular, the cleavage reactor (J) is connected downstream of the mixer (H) and the extraction phase separator (I). This results in the advantage that what is fed to the cleavage reactor (J) is the organic components after the phase separation, i.e. the organic raffinate (11), which means that the bottoms mixture in the cleavage reactor (J) which is removed via a conduit 21 is anhydrous and hence less corrosive. In addition, the recycling of by-products formed in the cleavage reactor (G) with the extract into the reactor (A) or into the reaction zone (E1) is avoided by this arrangement. The phase separation in the extraction phase separator (1) is also improved by this arrangement, for reasons including the fact that the viscosity of the continuous phase, i.e. of the organic raffinate (11), is lower and the difference in density between the two phases, i.e. the organic raffinate (11) and the aqueous extract (12), is higher by comparison with an extraction downstream of the cleavage reactor (J).

In a preferred configuration of the process, a substream of the organic raffinate (11) is fed to a cleavage reactor (J), where the mass flow ratio between the substream of the organic raffinate (11) and the total mass flow rate of the organic raffinate is in the range from 0.1 to 1.0, preferably in the range from 0.95 to 1.0. This results in the advantage that the high boilers can be cleaved and the cleavage products such as (meth)acrylic acid and n-butanol can be used again in the process as reactants.

In a preferred configuration of the process, the esterification takes place at a temperature in the range from 90 to 130° C., preferably in the range from 95 to 105° C., and at an absolute pressure in the range from 0.8 to 2.0 bar, preferably in the range from 1.0 to 1.5 bar. This results in the advantage that the conversion is at a maximum and the formation of secondary components is kept to a minimum.

In a preferred configuration of the process, a substream (8) of the high boiler bottoms output (23) is fed to the cleavage reactor (J) in a mass flow ratio to the high boiler substream (7) of the high boiler bottoms output (23) in the range from 0.0 to 10.0, preferably in the range from 0.1 to 1.0. This results in the advantage that there is sufficient catalyst for the cleavage reaction in the cleavage reactor (J).

In a preferred configuration of the process, a substream (9) of the high boiler bottoms output (23) is fed to the reactor (A) in a mass flow ratio to the total high boiler bottoms output (23) in the range from 0.1 to 0.99, preferably in the range from 0.85 to 0.95. This results in the advantage that the catalyst is returned and reused.

In a preferred configuration of the process, the high boiler bottoms output (23) has a water content in the range from 0.1% to 10.0% by weight, further preferably from 0.1% to less than 10.0% by weight, further preferably from 0.1% to less than 5% by weight, especially from 0.1% to 4.5% by weight. This results in the advantage that not too much water is present in the process and hence less energy is required and a lower level of secondary components is formed. At the same time, however, monophasic withdrawal of the high boiler bottoms output (23) and then, after addition of water in the mixer (H), a biphasic separation of the resulting mixture (10) is assured.

In a preferred configuration of the process, the high boiler bottoms output (23) has a content of oligomers and/or polymers in the range from 1% to 80% by weight, further preferably from 10% to 65% by weight, especially from 20% to 60% by weight. Oligomers and/or polymers are understood to mean molecules having a mass-average molar mass of more than 1000 g/mol. A content of oligomers and/or polymers of 80% by weight or less in the high boiler bottoms output (23) results in the advantage of a lower viscosity, such that the subsequent phase separation in the extraction phase separator (I) is improved. The mass flow ratio between the substream of the aqueous phase (18) and the high boiler substream (7) of the discharged high boiler bottoms output (23) or between the substream of the aqueous phase (26) and the high boiler substream (7) of the discharged high boiler bottoms output (23) can be reduced further.

In a preferred configuration of the process, the high boiler bottoms output (23) has a catalyst content in the range from 0.1% to 10.0% by weight. This results in the advantage that not too much catalyst has to be removed, and hence the process can proceed with greater energy efficiency and less catalyst can be used in the process.

In a preferred configuration of the process, the acidic catalyst comprises in the range from 0% to 100% by weight, preferably in the range from 80% to 100% by weight, more preferably in the range from 95% to 100% by weight, of p-toluenesulfonic acid. This results in the advantage that the esterification proceeds very efficiently because this catalyst has high selectivity, high reactivity and a high lifetime in this process.

In a further configuration of the process, the high boiler bottoms output (23) is monophasic. In this case, a substream of the aqueous phase (18) from the phase separator (G) and/or a substream of the aqueous phase (26) from the phase separator (D) is added to the mixer (H) in such an amount that the resulting mixture (10) is biphasic.

In a further configuration of the process, an external water is additionally added to the mixer (H). This is advantageous especially if the mass flow of the aqueous phase (18) and the phase separator (G) and/or the mass flow of the aqueous phase (26) from the phase separator (D) into the mixer (H) should be insufficient for a biphasic separation of the high boiler substream (7) of the high boiler bottoms output (23).

In a further configuration of the process, a substream of the organic phase (14) from the phase separator (G) is returned to the rectification column (E) with a reflux ratio based on the organic phase in the range from 0.1 to 1.0, and a substream of the aqueous phase (16) from the phase separator (G) with a reflux ratio based on the aqueous phase in the range from 1 to 10. This results in the advantage that less organic phase has to be discharged from the process and less aqueous phase has to be removed, and both the esterification and the removal in the rectification column (E) proceed in an energy-efficient manner. Moreover, a lower level of secondary components is formed.

In a further configuration of the process, the acidic catalyst is present in a concentration in the range from 0.1% to 10% by weight in the reaction zone (E1) of the rectification column (E) or in the resulting reaction output of the reactor (A). This results in the advantage that not too much catalyst has to be removed, and hence the process can proceed with greater energy efficiency and less catalyst can be used in the process.

In a further configuration of the process, a substream of the aqueous extract (12) is fed to the reactor (A) in a mass flow ratio to the total high boiler bottoms output (23) in the range from 0.01 to 0.5, preferably in the range from 0.01 to 0.3.

The invention will be elucidated in detail hereinafter with reference to the drawings. The drawings should be considered to be schematic diagrams. They do not constitute a limitation of the invention, for example with regard to specific dimensions or design variants.

LIST OF REFERENCE NUMBERS USED

Figure 1:
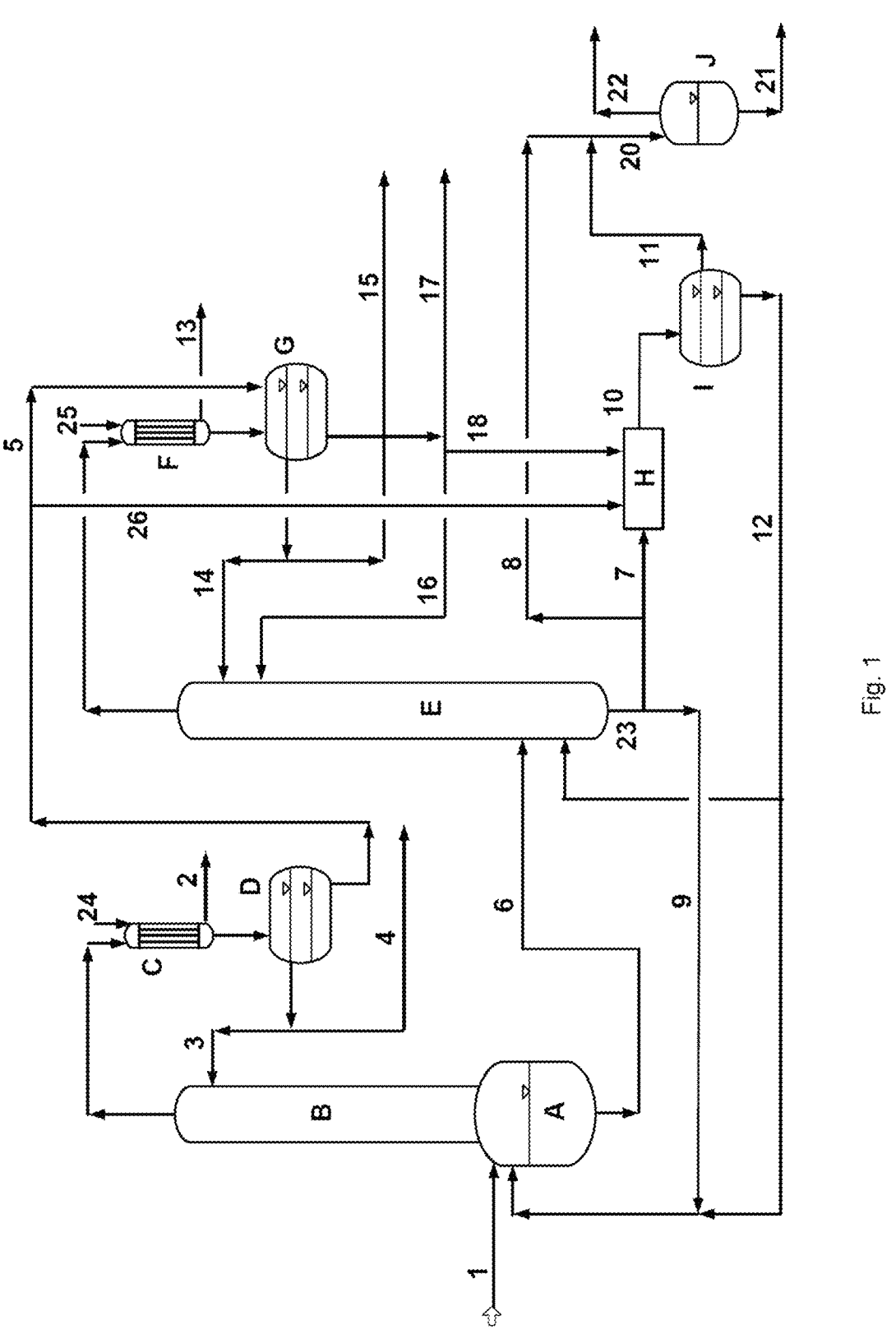
FIG. 1: A first embodiment of a process of the invention for continuously preparing n-butyl (meth)acrylate, in which a reactor A with a downstream rectification column E is used. In this case, a catalyst-comprising aqueous extract is recycled into the reactor A and/or into the rectification column E.

1 conduit for feeding in the reactant stream
2 residual vapor from the condenser C
3 conduit for recycling of the organic phase from the liquid-liquid phase separator D
4 conduit for discharging the organic phase from the liquid-liquid phase separator D
5 conduit for feeding the aqueous phase from the liquid-liquid phase separator D to the liquid-liquid phase separator G, or aqueous phase from the liquid-liquid phase separator D to the liquid-liquid phase separator G
6 conduit for feeding the resulting reaction output into the rectification column E
7 conduit for the substream of the high boiler bottoms output 23 to the mixer H or high boiler substream of the high boiler bottoms output 23 to the mixer H
8 conduit for the substream of the high boiler bottoms output 23 to the cleavage reactor J or substream of the high boiler bottoms output 23 to the cleavage reactor J
9 conduit for recycling of a substream of the high boiler bottoms output 23 to the reactor A or substream of the high boiler bottoms output 23 to the reactor A
10 resulting mixture from the mixer H
11 conduit for feeding organic raffinate from the extraction phase separator I to the cleavage reactor J or organic raffinate
12 conduit for recycling the aqueous extract from the extraction phase separator I to the reactor or to the rectification column E or aqueous extract
13 residual vapor from the condenser F
14 conduit for recycling the organic phase from the liquid-liquid phase separator G to the rectification column E, or organic phase from the liquid-liquid phase separator G
15 conduit for discharging a substream of the organic phase from the liquid-liquid phase separator G or crude product stream
16 conduit for recycling the aqueous phase from the liquid-liquid phase separator G to the rectification column E or aqueous phase from the liquid-liquid phase separator G
17 conduit for discharging a substream of the aqueous phase from the liquid-liquid phase separator G
18 conduit for feeding a substream of the aqueous phase from the liquid-liquid phase separator G to the mixer H, or aqueous phase from the liquid-liquid phase separator G
21 conduit for discharging the high boiler bottoms output of the cleavage reactor J
22 conduit for the discharge of the high boilers from the cleavage reactor J
23 conduit for the high boiler bottoms output of the rectification column E or high boiler bottoms output of the rectification column E
24 conduit for feeding the polymerization inhibitor stream to the condenser C
25 conduit for feeding the polymerization inhibitor stream to the condenser F
26 conduit for feeding the aqueous phase from the liquid-liquid phase separator D to the mixer H, or aqueous phase from the liquid-liquid phase separator D
A reactor
B column
C condenser
D phase separator
E rectification column
E1 reactor integrated into the rectification column
F condenser
G phase separator
H mixer
I extraction phase separator
J cleavage reactor FIG. 1 shows a schematic of a process flow diagram of a chemical engineering process according to a first embodiment of the process of the invention, in which a substream of the aqueous phase 18 from a liquid-liquid phase separator G is added to a mixer H.

A reactant mass flow comprising n-butanol, acrylic acid, PTZ and p-toluenesulfonic acid as esterification catalyst is fed to a reactor A through a conduit 1. A column B disposed above the reactor A separates a vapor mixture flowing out of the reactor A by means of its separating internals. A downstream condenser C, which may optionally be supplemented by a postcooler, at least partly condenses the vapor stream arising from the column B. A solution of the polymerization inhibitor PTZ is added to the condenser C via a conduit 24. The uncondensed fraction from the condenser C comprises low-boiling impurities and is drawn off in vaporous form via a conduit 2. The condensed vapor stream flows as condensate into a liquid-liquid phase separator D. The condensate separates therein into an aqueous phase and an organic phase. The aqueous phase comprising mainly water is guided through a conduit 5 from the liquid-liquid phase separator D to a liquid-liquid phase separator G. A further substream of the aqueous phase may in principle also serve as extractant and be fed through a conduit 26 from the liquid-liquid phase separator D to the mixer H.

A resulting reaction output comprising n-butyl acrylate, unconverted reactants and higher-boiling impurities inter alia is drawn off from the lower portion of the reactor A via a conduit 6 and fed to a rectification column E having separating internals. Water, n-butyl acrylate and alcohol inter alia are separated off in the rectification column E. The vapors exiting from the column are fed to a condenser F, which may optionally be supplemented by a postcooler, and partly condensed therein. A solution of the polymerization inhibitor PTZ is added to the condenser F via a conduit 25. The uncondensed fraction from the condenser F comprises low-boiling impurities and is drawn off in vaporous form via a conduit 13, whereas the resulting condensate flows into the liquid-liquid phase separator G. The condensate separates therein into an organic phase and an aqueous phase.

An organic phase comprising mainly n-butyl acrylate and n-butanol is partly returned as reflux via a conduit 14 back to the rectification column E, and the remainder is discharged via a conduit 15 for further workup. The aqueous phase comprising mainly water is partly returned as reflux via a conduit 16 back to the rectification column E, and partly conducted to a mixer H as extractant via a conduit 18, and the remainder is discharged via a conduit 17 for further workup.

Mainly higher-boiling impurities and the catalyst used are drawn off from the lower portion of the rectification column E via a conduit 23 and returned to the cleavage reactor J, to the mixer H and back to the reactor A via the downstream conduits 7, 8 and 9. In the mixer H, as extractant, the aqueous phase from the liquid-liquid phase separator G via the conduit 18 and/or the aqueous phase via the conduit 26 is mixed with the mass flow from the conduit 7 and fed to an extraction phase separator I via a conduit 10.

In the extraction phase separator I, the resultant mixture separates into an organic raffinate and a catalyst-comprising aqueous extract. The aqueous extract, comprising mainly water, is fed to the reactor A via a conduit 12. The organic raffinate is fed at least partly to a cleavage reactor J via a conduit 11 for further workup. The high boiler bottoms output is also fed at least partly to the cleavage reactor J via a conduit 8 for further workup. The bottoms output from the cleavage reactor J is discharged from the process via a conduit 21, whereas the gaseous substances are drawn off at the top of the cleavage reactor J via a conduit 22. Subsequently, the gaseous substances can be condensed and finally returned back to the reactor A.

Figure 2:
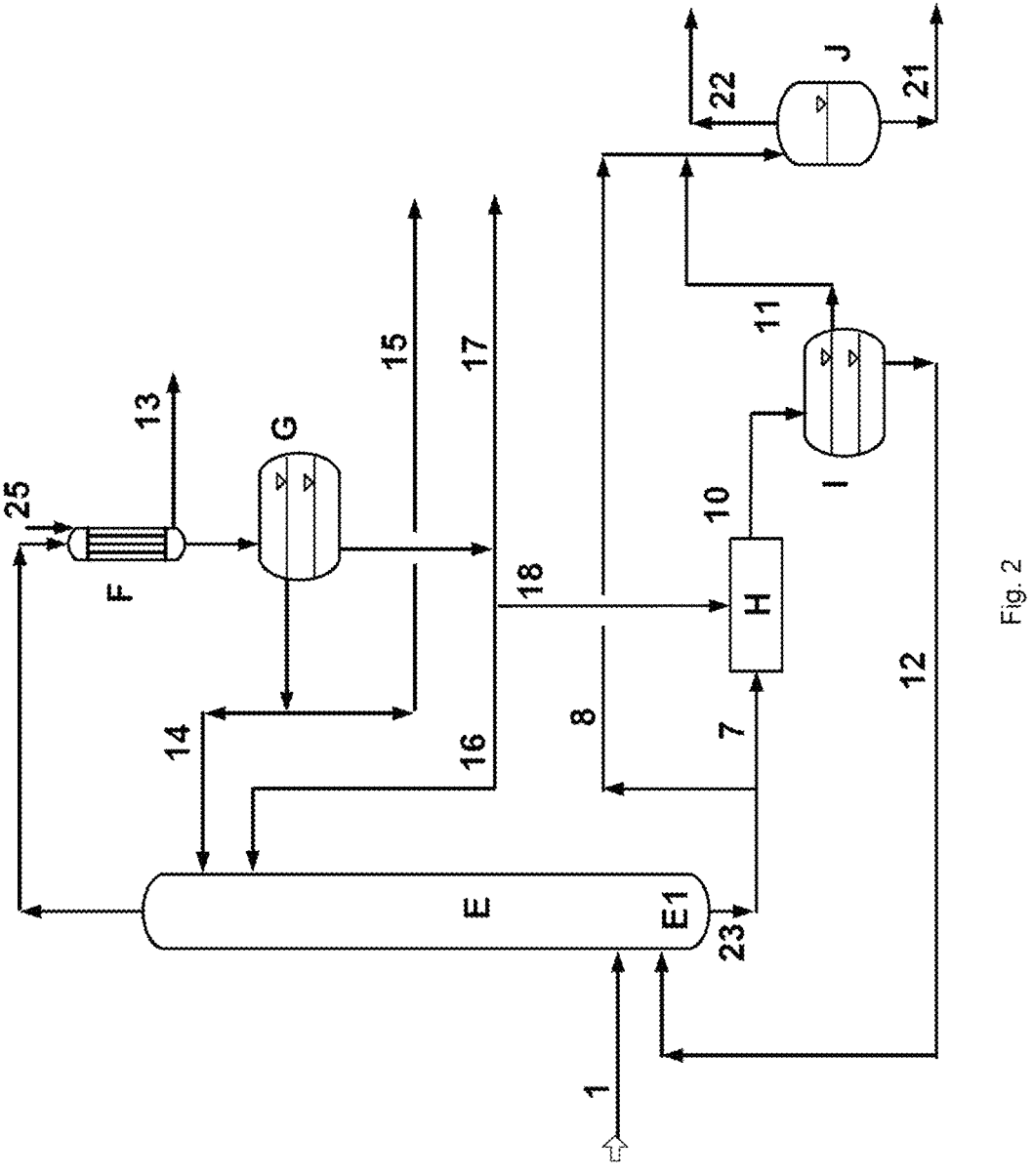
FIG. 2: A second embodiment of a process of the invention for continuously preparing n-butyl (meth)acrylate, in which a reaction zone E1 is integrated in the bottom region of a rectification column E. In this case, a catalyst-comprising aqueous extract is recycled into the rectification column E.

FIG. 2 shows a schematic of a process flow diagram of a chemical engineering process according to a second, alternative embodiment of the process of the invention, in which a substream of the aqueous phase 18 is added to a mixer H from a liquid-liquid phase separator G, wherein the reaction zone E1 is integrated into the bottom of the rectification column E in this embodiment by comparison with the first embodiment.

Figure 3:
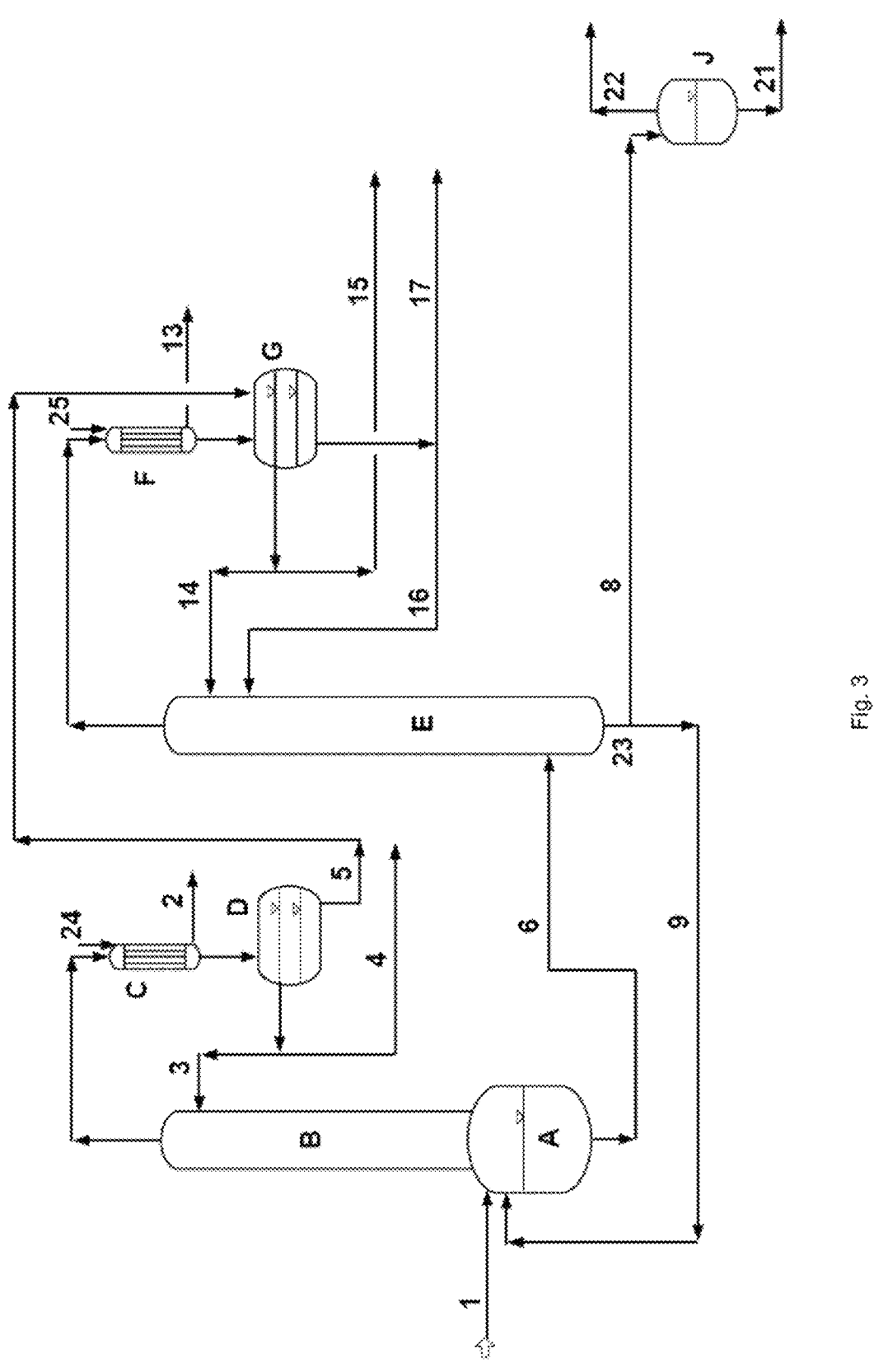
FIG. 3: A third embodiment of a process for continuously preparing n-butyl (meth)acrylate as a comparative example, in which a reactor A with a downstream rectification column E is used. In this case, there is no recycling of a catalyst-comprising aqueous extract into the reactor A and/or into the rectification column E.

FIG. 3 shows a schematic of a process flow diagram of a chemical engineering process as a comparative example, wherein there is no mixer H and no extraction phase separator I by comparison with the first embodiment, which means that no recycling of the aqueous extract from the extraction phase separator I to the reactor A is enabled.

EXAMPLES

The examples of the process that follow are simulated by thermodynamic simulations. For this purpose, the Aspen Plus® software (Aspen) is used, which can be found at the website https://www.aspentech.com (retrieved 15.07.2022). Aspen is an extensive simulation software package which is used for modeling, simulation and optimization of chemical processes and plants in industry. Aspen has extensive model databases for modelling of basic operations and substance databases for the physical properties of many different substances. The properties of mixtures are calculated by Aspen with the aid of different thermodynamic models from the physical data of the pure substances.

Comparative Example 1

A thermodynamic simulation of the overall plant according to FIG. 3 is conducted by Aspen and gives the following results:

A reactant stream is fed via a conduit 1 to a reactor A with a mass flow rate of 1000 kg/h, where the reactant stream is a mixture having the following composition:

n-Butanol: 582.2 kg/h
Acrylic acid: 413.9 kg/h
p-Toluenesulfonic acid: 3.9 kg/h.

A column B disposed above the reactor A separates a vapor mixture flowing out of the reactor A by means of its separating internals. A downstream condenser C at least partly condenses the vapor stream formed from column B.

A solution of the polymerization inhibitor is added via the conduit 24 to a condenser C with a mass flow rate of 2 kg/h, said solution of the polymerization inhibitor having the following composition:

n-Butyl acrylate: 98% by weight
Phenothiazine: 2% by weight.

The uncondensed fraction from the condenser C comprises low-boiling impurities and is drawn off in vaporous form via a conduit 2.

The esterification is conducted in the reactor A at a temperature of 105° C., a pressure of 470 mbar and a dwell time of 2 h.

27 kg/h of the organic phase is drawn off as organic distillate via a conduit 4 from a liquid-liquid phase separator D downstream of the condenser C, and 798 kg/h is returned to the column B as reflux via a conduit 3.

The organic phase as organic distillate has the following composition:

Water: 19.6% by weight
n-Butanol: 77.3% by weight
n-Butyl acrylate: 1.5% by weight
Acrylic acid: <0.01% by weight
n-Butyl acetate: 1.2% by weight
Phenothiazine: <0.01% by weight
Unknown: 0.4% by weight.

145 kg/h of the aqueous phase is guided via a conduit 5 from the liquid-liquid phase separator D to a liquid-liquid phase separator G. The aqueous phase has the following composition:

Water: 94.0% by weight
n-Butanol: 5.9% by weight
Unknown: 0.1% by weight.

In the lower portion of the reactor A, a resulting reaction output is drawn off via the conduit 6 with a mass flow rate of 1415 kg/h with the following composition, and fed to a rectification column E:

Water: 0.2% by weight
n-Butanol: 10.2% by weight
n-Butyl acrylate: 68.0% by weight
Acrylic acid: 5.0% by weight
n-Butyl acetate: 0.0% to 0.1% by weight
p-Toluenesulfonic acid 1.6% by weight
Phenothiazine 0.1% by weight
Unknown: 14.7% to 14.8% by weight.

In a rectification column E equipped with 13 theoretical plates, water, n-butanol and n-butyl acrylate are drawn off from the rectification column E in vaporous form overhead, condensed in a condenser F and then fed to a liquid-liquid phase separator G. In the top region of the column, the pressure is 1059 mbar and the temperature is 95° C.

A solution of the polymerization inhibitor is added via the conduit 25 to a condenser F with a mass flow rate of 2 kg/h, said solution of the polymerization inhibitor having the following composition:

n-Butyl acrylate: 98% by weight
Phenothiazine: 2% by weight.

803 kg/h of the organic phase is drawn off via the conduit 15 from the liquid-liquid phase separator G as organic distillate for further purification. A substream with a mass flow rate of 365 kg/h is returned to the rectification column E as reflux via the conduit 14.

The organic phase has the following composition:
Water: 2.7% by weight
n-Butanol: 16.8% by weight
n-Butyl acrylate: 80.3% by weight
Acrylic acid: <0.01% by weight
n-Butyl acetate: 0.1% by weight
Phenothiazine: <0.01% by weight
Unknown: 0.1% by weight.

83 kg/h of the aqueous phase is drawn off via conduit 17 from the liquid-liquid phase separator G as aqueous distillate. A substream with a mass flow rate of 724 kg/h of the aqueous phase is returned to the rectification column E as reflux via the conduit 16.

The aqueous phase has the following composition:
Water: 96.7% by weight
n-Butanol: 2.0% by weight
n-Butyl acrylate: 1.3% by weight
Unknown: <0.05% by weight.

In the lower portion of the rectification column E, a substream with a mass flow rate of 73 kg/h is conducted via a conduit 8 to a cleavage reactor J, and a substream with a mass flow rate of 585 kg/h via a conduit 9 back to the reactor A. The vapor mixture formed in the cleavage reactor J is removed via a conduit 22, whereas the bottoms mixture is removed via a conduit 21.

The bottoms mixture in the cleavage reactor J has the following composition:
Water: 3.1% by weight
n-Butanol: 4.3% by weight
n-Butyl acrylate: 21.4% by weight
Acrylic acid: 11.1% by weight
p-Toluenesulfonic acid 3.4% by weight
Phenothiazine: 0.2% by weight
Unknown: 56.5% by weight.

A content of oligomers and/or polymers is included in the unknowns.

Example 1

In this example 1, an inventive embodiment of the process for preparing n-butyl (meth)acrylate according to FIG. 1 is simulated by the Aspen software. The simulation gives the following results:

A reactant stream is fed via a conduit 1 to a reactor A with a mass flow rate of 1000 kg/h, where the reactant stream has the following composition:

n-Butanol: 584.3 kg/h
Acrylic acid: 414.4 kg/h
p-Toluenesulfonic acid: 1.3 kg/h.

The esterification in the reactor A is conducted at a temperature of 105° C., an absolute pressure of 470 mbar and a dwell time of 2 hours.

A column B disposed above the reactor A separates a vapor mixture flowing out of the reactor A by means of its separating internals. A downstream condenser C at least partly condenses the vapor stream formed from column B.

A solution of the polymerization inhibitor is added via the conduit 24 to the condenser C with a mass flow rate of 2 kg/h, said solution of the polymerization inhibitor having the following composition:

n-Butyl acrylate: 98% by weight
Phenothiazine: 2% by weight.

The uncondensed fraction from the condenser C comprises low-boiling impurities and is drawn off in vaporous form via a conduit 2.

27 kg/h of the organic phase is drawn off as organic distillate via a conduit 4 from a liquid-liquid phase separator D downstream of the condenser C, and 934 kg/h is returned to the column B as reflux via a conduit 3.

The organic phase has the following composition:
Water: 19.5% by weight
n-Butanol: 77.0% by weight
n-Butyl acrylate: 1.7% by weight
Acrylic acid: <0.01% by weight
n-Butyl acetate: 1.4% by weight
Phenothiazine: <0.01% by weight
Unknown: 0.4% by weight.

An aqueous phase with a mass flow rate of 155 kg/h is conducted via the conduit 5 from the liquid-liquid phase separator D to a liquid-liquid phase separator G.

The aqueous phase has the following composition:
Water: 94.0% by weight
n-Butanol: 5.9% by weight
Unknown: 0.1% by weight.

In the lower portion of the reactor A, a liquid mixture with a mass flow rate of 1422 kg/h is drawn off via the conduit 6 with the following composition, and fed to a rectification column E:

Water: 0.2% by weight
n-Butanol: 10.2% by weight
n-Butyl acrylate: 68.0% by weight
Acrylic acid: 5.0% by weight
n-Butyl acetate: 0.0% to 0.1% by weight
p-Toluenesulfonic acid 1.6% by weight
Phenothiazine 0.2% by weight
Unknown: 14.7% to 14.8% by weight.

In a rectification column E equipped with 13 theoretical plates, water, n-butanol and n-butyl acrylate are drawn off from the rectification column E in vaporous form overhead, condensed in a condenser F and then fed to a liquid-liquid phase separator G. In the top region of the rectification column E, the absolute pressure is 1059 mbar and the temperature is 95° C.

A solution of the polymerization inhibitor is added via a conduit 25 to a condenser F with a mass flow rate of 2 kg/h, said solution of the polymerization inhibitor having the following composition:

n-Butyl acrylate: 98% by weight
Phenothiazine: 2% by weight.

The organic phase with a mass flow rate of 807 kg/h is drawn off from the liquid-liquid phase separator G via a conduit 15 as organic distillate for further purification. A substream with a mass flow rate of 367 kg/h is returned to the rectification column E as reflux via a conduit 14.

The organic phase has the following composition:

Water: 2.6% by weight
n-Butanol: 16.7% by weight
n-Butyl acrylate: 80.5% by weight
Acrylic acid: <0.01% by weight
n-Butyl acetate: 0.1% by weight
Phenothiazine: <0.01% by weight
Unknown: 0.1% by weight.

A mass flow rate of 101 kg/h of the aqueous phase is drawn off from the liquid-liquid phase separator G as aqueous distillate via a conduit 17 for further purification. A substream with a mass flow rate of 728 kg/h is returned to the rectification column E as reflux via a conduit 16.

A further substream of the aqueous phase is conducted to a mixer H via a conduit 18 with a mass flow rate of 10 kg/h as extractant for the catalyst extraction.

The aqueous phase has the following composition:

Water: 96.7% by weight
n-Butanol: 2.0% by weight
n-Butyl acrylate: 1.3% by weight
Unknown: <0.05% by weight.

In the lower portion of the rectification column E, a substream is conducted to the mixer H via a conduit 7 with a mass flow rate of 49 kg/h, a substream with a mass flow rate of 24 kg/h via a conduit 8 to a cleavage reactor J, and a substream with a mass flow rate of 588 kg/h via a conduit 9 back to the reactor A.

The liquid mixture has the following composition:

Water: 3.1% by weight
n-Butanol: 4.3% by weight
n-Butyl acrylate: 21.7% by weight
Acrylic acid: 11.1% by weight
p-Toluenesulfonic acid 3.4% by weight
Phenothiazine: 0.4% by weight
Unknown: 56.0% by weight.

The content of oligomers and/or polymers is included in the unknowns.

In the mixer H, the substream from the rectification column E comprising the catalyst and higher-boiling impurities via the conduit 7 is mixed with a substream 18 from the liquid-liquid phase separator G comprising the water extractant in a phase ratio of 0.2 kg/kg, and fed via a conduit 10 to an extraction phase separator I, where the phase ratio is calculated by the addition of the mass flow rate of the aqueous phase from the high boiler substream 7 and the mass flow rate of the water extractant from the substream 18, where the value from the addition is divided by the mass flow rate of the organic phase of the substream 7 and the mass flow rate of the organic phase of the substream 18.

45 kg/h of the organic raffinate is removed as organic mixture from the extraction phase separator I via a conduit 11 and added to the cleavage reactor J for further purification. The vapor mixture formed in the cleavage reactor J is removed via a conduit 22, whereas the bottoms mixture is removed via a conduit 21.

The organic raffinate has the following composition:

Water: 2.0% by weight
n-Butanol: 4.9% by weight
n-Butyl acrylate: 23.8% by weight
Acrylic acid: 9.1% by weight
p-Toluenesulfonic acid <0.05% by weight
Phenothiazine: 0.2% by weight
Unknown: 59.9% by weight.

The content of oligomers and polymers is included in the unknowns.

The aqueous extract is conducted from the extraction phase separator I back to the reactor A with a mass flow rate of 14 kg/h via a conduit 12.

The aqueous extract has the following composition:

Water: 71.2% by weight
n-Butanol: 0.7% by weight
n-Butyl acrylate: 0.9% by weight
Acrylic acid: 9.9% by weight
p-Toluenesulfonic acid 11.9% by weight
Phenothiazine: 0.7% by weight
Unknown: 4.7% by weight.

It can be stated in summary from the two examples that the following is apparent with the same catalyst concentration in the reactor A:

The catalyst-comprising reactant stream which is fed to the reactor A via the conduit 1 has a lower catalyst concentration in inventive example 1 than in comparative example 1. Thus, in inventive example 1, a mass flow rate of 1.3 kg/h of new catalyst is fed to the conduit 1, whereas, in comparative example 1, a mass flow rate of 3.9 kg/h of new catalyst is fed to the conduit 1.

This is because, in example 1, the aqueous extract 12 is returned to the reactor A with a mass flow rate of 14 kg/h, where the catalyst concentration is 11.9% by weight. In example 1, there is a phase separation since the phase ratio between the aqueous phase 18 and the high boiler substream 7 of the high boiler bottoms output 23 that arises at the outlet from the mixer H is 0.2 kg/kg, whereas, in comparative example 1, there is no mixer (H) and the water concentration in the high boiler bottoms output 23 is also only 0.03 kg/kg. There is thus no phase separation in comparative example 1.

As a result, there is a saving of 66.7% of the amount of catalyst in inventive example 1.

In addition, the influence of the arrangement of a cleavage reactor J in the process was examined experimentally.

Example 2

In example 2, the cleavage reactor J, analogously to example 1, was connected downstream of the mixer H and the extraction phase separator I. A high boiler substream 7 of the high boiler bottoms output 23 from the bottom of the rectification column E was fed to the mixer H. The viscosity of the organic raffinate 11 which was taken from the extraction phase separator I and fed to the cleavage reactor J was 0.7 mPas. A substream 18 from the liquid-liquid phase separator G which comprises the water extractant was used in the mixer H with a mass flow ratio between the substream of the aqueous phase 18 and the high boiler substream 7 of the discharged high boiler bottoms output 23 within a range from 0.13 to 0.34 kg/kg. The separation time in the extraction phase separator I was 60 s and the difference in density was 100 kg/m$^3$.

Example 3

In example 3, the cleavage reactor J was connected upstream of the mixer H, and a substream 8 (analogously to

19

FIG. 3) of the high boiler bottoms output 23 from the bottom of the rectification column E was first fed to the cleavage reactor J. The high boiler bottoms output 21 from the cleavage reactor J was then fed to the mixer H, downstream of which was connected the extraction phase separator I. The viscosity of the organic raffinate 11 which was taken here from the extraction phase separator I was 30 mPas. A substream 18 from the liquid-liquid phase separator G which comprises the water extractant was used in the mixer H with a mass flow ratio between the substream of the aqueous phase 18 and the high boiler bottoms output 21 from the cleavage reactor J of 1 kg/kg. The separation time in the extraction phase separator I was 240 to 300 s and the difference in density was low at 12 kg/m³.

The invention claimed is:

1. A process for continuously preparing n-butyl (meth) acrylate by reacting (meth)acrylic acid with n-butanol in the presence of an acidic catalyst and a polymerization inhibitor, comprising the steps of:

performing an esterification within a reactor A with a column B on top, where the (meth)acrylic acid and n-butanol components are in a molar ratio in the range from 1.0:1.0 to 1.0:2.0, and where the esterification takes place at a temperature in the range from 80 to 150° C., and at an absolute pressure in the range from 0.2 to 5.0 bar, as a result of which a resulting bottom reaction output is obtained, while a vapor stream is obtained at the top of the column B, discharging the vapor stream at the top of the column B, condensing the vapor stream in a condenser C to form an organic phase and an aqueous phase, separating the organic phase from the aqueous phase by means of a phase separator D, feeding the resulting reaction output into a rectification column E, separating off the following azeotropes within the rectification column E:

a) water and n-butyl (meth)acrylate,
b) n-butanol and n-butyl (meth)acrylate,
c) n-butanol and water,
d) n-butanol, n-butyl (meth)acrylate and water, where the rectification column E is operated at a bottom temperature in the range from 80 to 150° C. and at a temperature at the top in the range from 70 to 130° C. and at an absolute pressure in the range from 0.2 to 5 bar, discharging a gas stream enriched by the azeotropes at the top of the rectification column E, condensing the gas stream in a condenser F to form an n-butyl (meth)acrylate-enriched organic phase and an aqueous phase, separating the organic phase from the aqueous phase by means of a phase separator G, removing at least a portion of the organic phase from the phase separator G, where this removed portion of the n-butyl (meth)acrylate-enriched organic phase constitutes the crude product stream, discharging a high boiler bottoms output from the bottom of the rectification column E, where the mass flow ratio between the high boiler bottoms output and the (meth) acrylic acid fed to the reactor A as reactant is in the range from 0.5 to 5, feeding a high boiler substream of the discharged high boiler bottoms output into a mixer H, where the mass flow ratio between the high boiler substream and the high boiler bottoms output is in the range from 0.01 to 0.50,

feeding a mixture that results from the mixer H into a downstream extraction phase separator I, separating off the mixture in the extraction phase separator I to obtain an organic raffinate and a catalyst-comprising aqueous extract, where the aqueous extract is recycled at least partly to the reactor A or to the rectification column E, wherein a substream of the organic raffinate is fed to a cleavage reactor J, where the mass flow ratio between the substream of the organic raffinate and the total mass flow rate of the organic raffinate is in the range from 0.1 to 1.0, and wherein a substream of the aqueous phase from the phase separator G, a substream of the aqueous phase from the phase separator D or a substream of the aqueous phase from the phase separator D is fed to the phase separator G and then a substream of the aqueous phase from this phase separator G is fed to the mixer H, where the mass flow ratio between the substream of the aqueous phase and the high boiler substream of the discharged high boiler bottoms output is in the range from 0.08 to 0.5, and where the mass flow ratio between the substream of the aqueous phase and the high boiler substream of the discharged high boiler bottoms output is in the range from 0.08 to 0.5.

2. A process for continuously preparing n-butyl (meth) acrylate by reacting (meth)acrylic acid with n-butanol in the presence of an acidic catalyst and a polymerization inhibitor, comprising the steps of:

performing an esterification in a reaction zone, where the reaction zone is in the bottom of a rectification column E, where the (meth)acrylic acid and n-butanol components are in a molar ratio in the range from 1.0:1.0 to 1.0:2.0, and where the esterification takes place at a temperature in the range from 80 to 150° C., and at an absolute pressure in the range from 0.2 to 5.0 bar, separating off the following azeotropes that form as a result of the esterification:

a) water and n-butyl (meth)acrylate,
b) n-butanol and n-butyl (meth)acrylate,
c) n-butanol and water,
d) n-butanol, n-butyl (meth)acrylate and water, where the removal also takes place by means of the rectification column E, which is operated at a bottom temperature in the range from 80 to 150° C. and at a temperature at the top in the range from 70 to 130° C. and at an absolute pressure in the range from 0.2 to 5 bar, discharging a gas stream enriched by the azeotropes at the top of the rectification column E, condensing the gas stream in a condenser F to form an n-butyl (meth)acrylate-enriched organic phase and an aqueous phase, separating the organic phase from the aqueous phase by means of a phase separator G, removing at least a portion of the organic phase and the phase separator G, where this removed portion of the n-butyl (meth)acrylate-enriched organic phase constitutes the crude product stream, discharging a high boiler bottoms output from the bottom of the rectification column E, where the mass flow ratio between the high boiler bottoms output and the (meth) acrylic acid fed to the reaction zone as reactant is in the range from 0.05 to 0.5, feeding a high boiler substream of the discharged high boiler bottoms output into a mixer H, where the mass flow ratio between the high boiler substream and the high boiler bottoms output is in the range from 0.01 to 1.0, feeding a mixture that results from the mixer H into a downstream extraction phase separator I, separating off the mixture in the extraction phase separator I to obtain an organic raffinate and a catalyst-comprising aqueous extract, where the aqueous extract is recycled at least partly to the rectification column E, wherein a substream of the organic raffinate is fed to a cleavage reactor J, where the mass flow ratio between the substream of the organic raffinate and the total mass flow rate of the organic raffinate is in the range from 0.1 to 1.0, and wherein a substream of the aqueous phase from the phase separator G is fed to the mixer H, where the mass flow ratio between the substream of the aqueous phase from the phase separator G and the high boiler substream of the discharged high boiler bottoms output is in the range from 0.08 to 0.5.

3. The process according to claim 1, wherein the resulting mixture from the mixer H is at a temperature in the range from 20 to 100° C. at the outlet of the mixer H.

4. The process according to claim 1, wherein a substream of the aqueous extract is returned to the reactor A, where the mass flow ratio between the substream of the aqueous extract and the total mass flow rate of the aqueous extract is in the range from 0.1 to 1.0.

5. The process according to claim 1, wherein there is added to the high boiler substream of the discharged high boiler bottoms output in the mixer H such a mass flow rate of the substream of the aqueous phase from the phase separator G or of the substream of the aqueous phase from the phase separator D that a phase ratio between the aqueous extract to be obtained and the organic raffinate to be obtained in the range from 0.08 to 0.5 kg/kg is achieved.

6. The process according to claim 1, wherein a substream of the high boiler bottoms output is fed to the cleavage reactor J in a mass flow ratio to the high boiler substream of the high boiler bottoms output in the range from 0.0 to 10.0.

7. The process according to claim 1, wherein the high boiler bottoms output has a water content in the range from 0.1% to 10.0% by weight.

8. The process according to claim 1, wherein the high boiler bottoms output has a catalyst content in the range from 0.1% to 10.0% by weight.

9. The process according to claim 1, wherein the acidic catalyst comprises in the range from 0% to 100% by weight of p-toluenesulfonic acid.

10. The process according to claim 1, wherein the high boiler bottoms output is monophasic.

11. The process according to claim 1, wherein a substream of the organic phase from the phase separator G is returned to the rectification column E with a reflux ratio based on the organic phase in the range from 0.1 to 1.0, and a substream of the aqueous phase from the phase separator G with a reflux ratio based on the aqueous phase in the range from 1 to 10.

12. The process according to claim 1, wherein the acidic catalyst is present in a concentration in the range from 0.1% to 10.0% by weight in the resulting reaction output of the reactor A.

13. The process according to claim 1, wherein an external water is additionally added to the mixer H.

* * * * *